United States Patent
Lai et al.

(10) Patent No.: US 8,956,580 B2
(45) Date of Patent: Feb. 17, 2015

(54) ANALYSIS CARTRIDGE

(71) Applicant: Lite-On IT Corporation, Taipei (TW)

(72) Inventors: Cheng-Chang Lai, Hsinchu (TW); Fu-Chun Huang, Hsinchu (TW); Yuh-Jiuan Lin, Hsinchu (TW)

(73) Assignee: Lite-On Technology Corporation, Taipei (TW)

( * ) Notice: Subject to any disclaimer, the term of this patent is extended or adjusted under 35 U.S.C. 154(b) by 101 days.

(21) Appl. No.: 13/740,925

(22) Filed: Jan. 14, 2013

(65) Prior Publication Data

US 2013/0309149 A1 Nov. 21, 2013

(30) Foreign Application Priority Data

May 18, 2012 (CN) .......................... 2012 1 0155013

(51) Int. Cl.
- *B01L 3/00* (2006.01)
- *G01N 35/00* (2006.01)
- *G01N 35/04* (2006.01)

(52) U.S. Cl.
CPC ................. *B01L 3/508* (2013.01); *B01L 3/523* (2013.01); *B01L 3/5027* (2013.01); *G01N 2035/00495* (2013.01); *G01N 2035/00158* (2013.01); *G01N 2035/0405* (2013.01); *B01L 2200/0684* (2013.01); *B01L 2200/0689* (2013.01); *B01L 2200/141* (2013.01); *B01L 2300/044* (2013.01); *B01L 2300/0806* (2013.01); *B01L 2300/0864* (2013.01); *B01L 2300/0867* (2013.01); *B01L 2400/0409* (2013.01)
USPC ............. 422/554; 422/72; 422/415; 422/501; 422/506; 422/548; 422/559; 422/568; 435/286.4; 435/286.5

(58) Field of Classification Search
None
See application file for complete search history.

(56) References Cited

U.S. PATENT DOCUMENTS

| | | | |
|---|---|---|---|
| 5,061,381 A | 10/1991 | Burd | |
| 5,304,348 A | 4/1994 | Burd et al. | |
| 5,457,053 A | 10/1995 | Burd et al. | |
| 6,283,587 B1 * | 9/2001 | Umemura | ....................... 347/86 |
| 2007/0059817 A1 | 3/2007 | Aoyagi | |
| 2012/0270305 A1 | 10/2012 | Reed et al. | |

* cited by examiner

*Primary Examiner* — Jill Warden
*Assistant Examiner* — Timothy G Kingan
(74) *Attorney, Agent, or Firm* — Rabin & Berdo, P.C.

(57) ABSTRACT

An analysis cartridge comprising a cartridge body, a first cover, a liquid storage box and a sealing film is disclosed. The cartridge body has an accommodation portion and a first side and a second side opposite to the first side. The first cover covers the first side or the second side of the cartridge body and has a first through hole. The liquid storage box is disposed in the accommodation portion and has a liquid through hole. The sealing film seals the liquid through hole of the said liquid storage box and passes through the first through hole of the first cover, wherein the liquid through hole is exposed by removing the sealing film.

12 Claims, 5 Drawing Sheets

ANALYSIS CARTRIDGE

This application claims the benefit of People's Republic of China application Serial No. 201210155013.7, filed May 18, 2012, the subject matter of which is incorporated herein by reference.

BACKGROUND OF THE INVENTION

1. Field of the Invention

The invention relates in general to an analysis cartridge, and more particularly to the design of a sealing film of an analysis cartridge.

2. Description of the Related Art

The in vitro diagnostic testing process comprises the following operation sequence: (1) a test specimen is infused; (2) the test specimen is diluted; (3) the test specimen is mixed with a reagent; (4) an optical signal is measured. The main purpose of diluting the test specimen is for reducing the disruptor and increasing the volume of the specimen so that a multi-objective test can be performed on a tiny quantity of test specimen. Therefore, the diluent will be mixed with the test specimen according to a particular proportion.

Of the products currently available in the market, a diluent box pre-filled with a diluent is packaged in an analysis cartridge. After the analysis cartridge is loaded into an analyzer, the mechanism design of the analyzer opens an opening of the diluent box for allowing the diluent pre-filled in the diluent box to flow out the diluent box to be mixed with the test specimen in the analysis cartridge so that the test specimen can be diluted.

However, the procedure of opening the diluent box requires a complicated mechanism design, which not only increases the operation complexity, but further increases the size and weight of the analyzer.

SUMMARY OF THE INVENTION

The invention is directed to an analysis cartridge, which dispenses with a mechanism of opening a liquid through hole of a liquid storage box so as to effectively reduce cost and increase market competiveness.

According to an embodiment of the present invention, an analysis cartridge comprising a cartridge body, a first cover, a liquid storage box and a sealing film is disclosed. The cartridge body has an accommodation portion, and a first side and a second side opposite to the first side. The first cover covers the first side or the second side of the cartridge body and has a first through hole. The liquid storage box is disposed within the accommodation portion and has a liquid through hole. The sealing film seals the liquid through hole of the said liquid storage box and passes through the first through hole of the first cover, wherein the liquid through hole is exposed by removing the sealing film.

According to another embodiment of the present invention, an analysis cartridge comprising a cartridge body, a liquid storage box and a sealing film is disclosed. The cartridge body has an accommodation portion, and a first side and a second side opposite to the first side. The liquid storage box is disposed within the accommodation portion and has a liquid through hole. The liquid storage box comprises a liquid storage tank having an opening and a tank cover covering the opening of the liquid storage tank, and the liquid through hole is formed on the bottom of the liquid storage tank. The sealing film seals the liquid through hole, wherein the liquid through hole is exposed by removing the sealing film.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
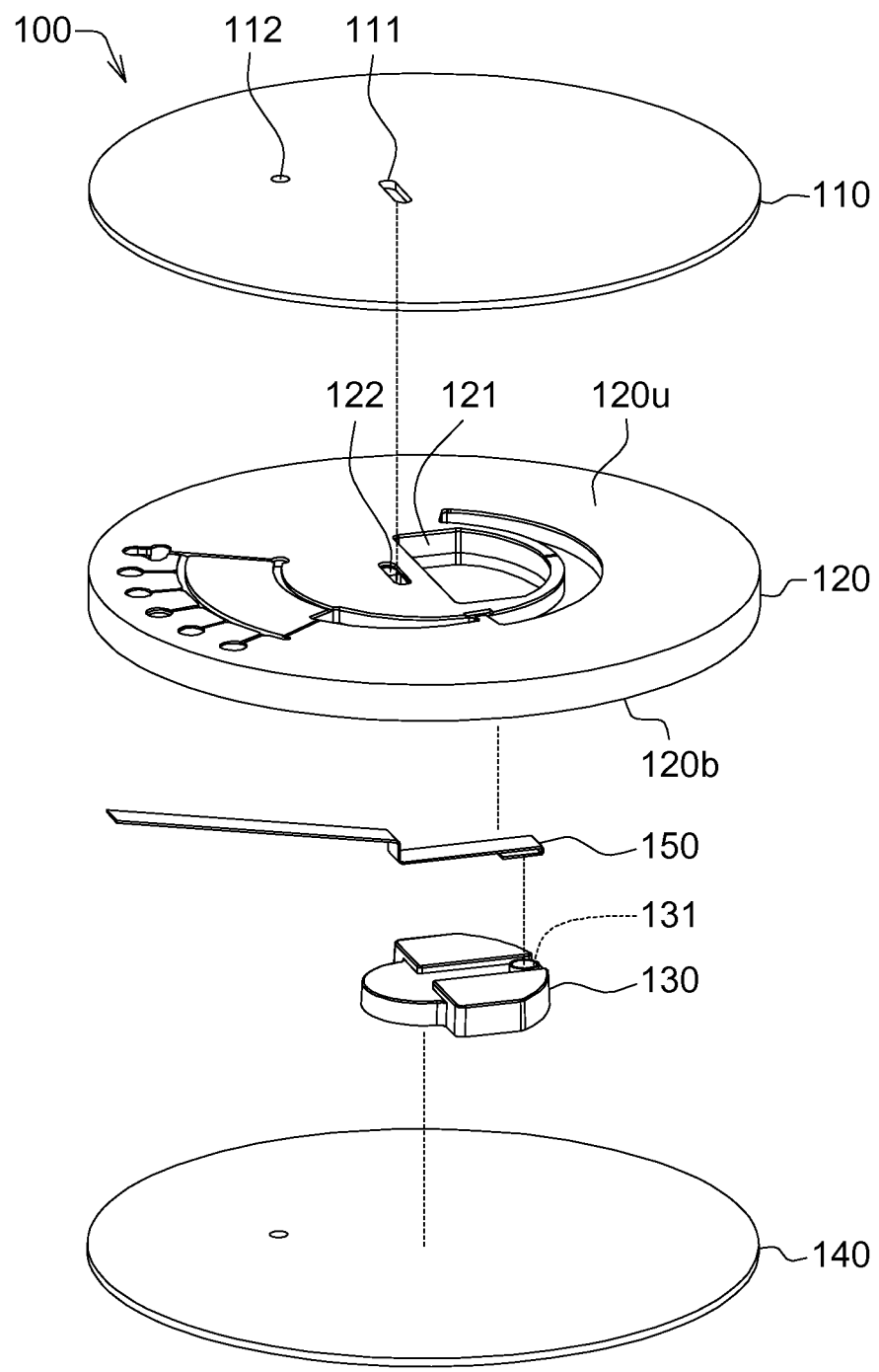
FIG. 1 shows an explosion diagram of an analysis cartridge according to an embodiment of the invention.

Referring to FIG. 1, an explosion diagram of an analysis cartridge according to an embodiment of the invention is shown. The analysis cartridge 100 comprises a first cover 110, a cartridge body 120, a liquid storage box 130, a second cover 140 and a sealing film 150.

The first cover 110 covers a first side 120u of the cartridge body 120 and has a first through hole 111. The first cover 110 may be formed by a high polymer such as polypropylene (PP) or polymethylmethacrylate (PMMA). Under such design, the first cover 110 may be bonded to the cartridge body 120 by hot melting method or ultra-sound bonding technology. Alternatively, the first cover 110 may be formed by an adhesive material such as an adhesive tape. Under such design, the first cover 110 may be adhered on the cartridge body 120.

The cartridge body 120 has an accommodation portion 121, a second through hole 122, and a first side 120u and a second side 120b opposite to the first side 120u. The cartridge body 120 may be formed by plastics such as polypropylene.

The liquid storage box 130, used for storing a diluent, can be contained within the accommodation portion 121 of the cartridge body 120. The liquid storage box 130 has a liquid through hole 131 via which the diluent flows out the liquid storage box 130 to be mixed with the test specimen. The sealing film 150 seals the liquid through hole 131 of the liquid storage box 130 to avoid the diluent flowing out when analysis is not performed.

Figure 2:
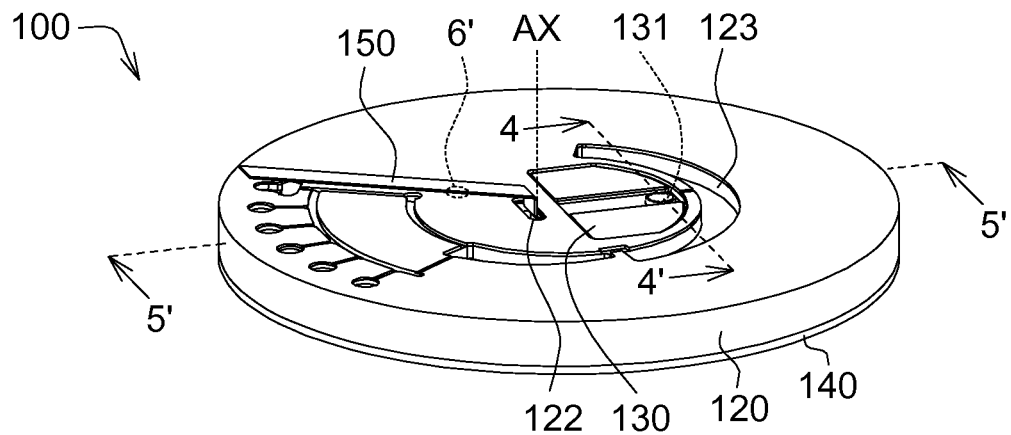
FIG. 2 shows an assembly diagram of a cartridge body, a liquid storage box, a second cover and a sealing film of FIG. 1.

Referring to FIG. 2, an assembly diagram of a cartridge body, a liquid storage box, a second cover and a sealing film of FIG. 1 is shown. The accommodation portion 121 may contain the liquid storage box 130. When analysis is not performed, the liquid through hole 131 of the liquid storage box 130 is sealed by the sealing film 150 to avoid the diluent L (FIG. 4) inside the liquid storage box 130 flowing out via the liquid through hole 131.

Figure 3:
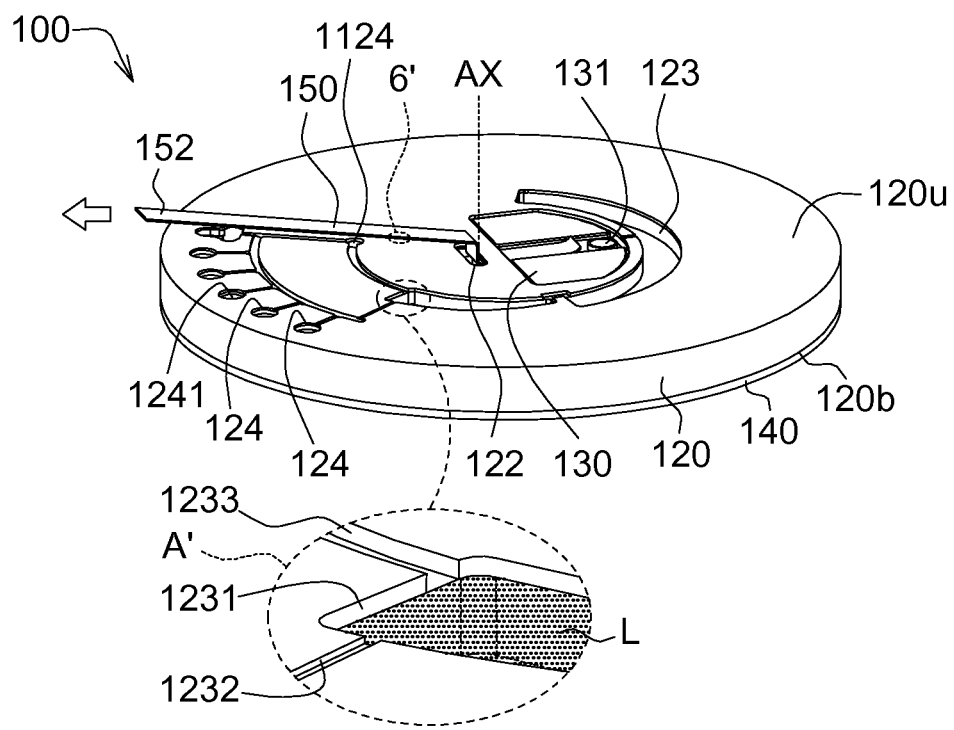
FIG. 3 shows a schematic diagram of the sealing film of FIG. 2 being torn apart and exposing the liquid through hole.

Referring to FIG. 3, a schematic diagram of the sealing film of FIG. 2 being torn apart and exposing the liquid through hole is shown. When analysis is performed, the operator may pull another terminal 152 of the sealing film 150 for exposing the sealed liquid through hole 131. Then, after the analysis cartridge 100 is loaded into an analyzer (not illustrated), the analyzer drives the analysis cartridge 100 to rotate around the axis AX, so that the diluent L stored in the liquid storage box 130 (FIG. 4) is driven by a centrifugal force to flow out and enter liquid channel 123 via the exposed liquid through hole 131. In addition, the axis AX is such as the center of the analysis cartridge 100.

The cartridge body 120 further has at least one reaction chamber 124, wherein the liquid channel 123 interconnects the reaction chamber 124 with the liquid through hole 131 of the liquid storage box 130, such that the diluent L inside the liquid storage box 130 may flow to the reaction chamber 124 via the liquid through hole 131 and the liquid channel 123 to react with the reactive substance 1241 stored in the reaction chamber 124.

Figure 5:
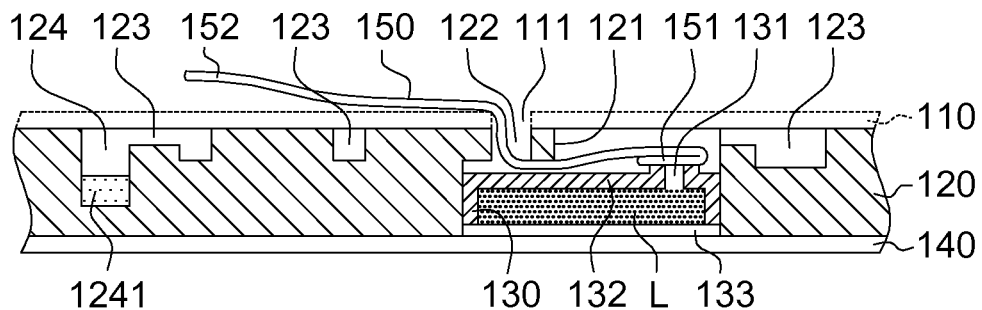
FIG. 5 shows a cross-sectional view along a direction 5-5' of FIG. 2.

In the present embodiment, the reaction chamber 124 is realized by a blind hole (referring to FIG. 5). In another embodiment, the reaction chamber 124 is realized by a through hole. Despite the reaction chamber 124 is a through hole, the reactive substance 1241 inside the reaction chamber 124 is blocked by the second cover 140 (FIG. 5) and will not flow out.

As indicated in an enlargement diagram of FIG. 3, the liquid channel 123 has a liquid accumulation tank 1231, a first distribution channel 1232 and a second distribution channel 1233, wherein the first distribution channel 1232 and the second distribution channel 1233 are connected to the liquid accumulation tank 1231. Through the design of the distance between the first distribution channel 1232 and the axis AX, the flow of the diluent L entering the first distribution channel 1232 from the liquid accumulation tank 1231 can be controlled, so that the predetermined or expected reaction between the diluent L and the reactive substance 1241 inside the reaction chamber 124 can be achieved.

Since the distance between the first distribution channel 1232 and the axis AX is larger than that between the second distribution channel 1233 and the axis AX, the centrifugal force driving the diluent L in the first distribution channel 1232 is larger than the centrifugal force driving the diluent L in the second distribution channel 1233, making most or all of the diluent L inside the liquid accumulation tank 1231 enter the first distribution channel 1232 and flow to the reaction chamber 124. In addition, the second distribution channel 1233 interconnects with the ventilation hole 112 of the first cover 110, so that the gas inside the liquid channel 123 may be discharged off the analysis cartridge 100 through the second distribution channel 1233 and the ventilation hole 112 of the first cover 110 (FIG. 1).

Figure 4:
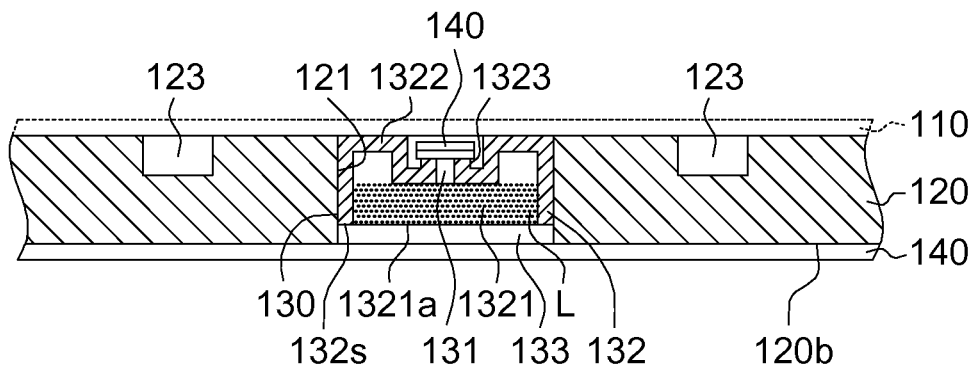
FIG. 4 shows a cross-sectional view along a direction 4-4' of FIG. 2.

Referring to FIG. 4, a cross-sectional view along a direction 4-4' of FIG. 2 is shown. The liquid storage box 130 is disposed within the accommodation portion 121. In an embodiment of the invention, the outer diameter of the liquid storage box 130 is larger than the inner diameter of the accommodation portion 121, such that the liquid storage box 130 is tightly located within the accommodation portion 121. In another embodiment, the liquid storage box 130 is bonded to the first cover 110 by using such as hot melting method or ultra-sound bonding technology. Under such design, the outer diameter of the liquid storage box 130 does not have to be larger than the inner diameter of the accommodation portion 121. Instead, the outer diameter of the liquid storage box 130 may be smaller than or equal to the inner diameter of the accommodation portion 121.

The liquid storage box 130 comprises a box body 132 and a tank cover 133. The box body 132 further has a liquid storage tank 1321 and a tank bottom 1322. The liquid storage tank 1321 extends to the tank bottom 1322 from the terminal surface 132s. The tank bottom 1322 faces the first cover 110. The liquid through hole 131 penetrates the tank bottom 1322 and interconnects with the liquid storage tank 1321. The tank cover 133 is adhered on a terminal surface 132s of the box body 132 to cover an opening 1321a of the liquid storage tank 1321 which is exposed from the terminal surface 132s. In other words, the liquid storage tank 1321 has an opening facing the second side 120b of the cartridge body 120, and the tank cover 133 covers the opening of the liquid storage tank 1321. The tank cover 133 is formed by a metal or a high polymer, wherein the metal is such as aluminum, and the high polymer is such as plastics.

In the present embodiment, the tank bottom 1322 of the box body 132 has a flange 1323, and the liquid through hole 131 penetrates the flange 1323. Through the design of the flange 1323, the sealing film 150 seals the liquid through hole 131 more tightly.

The second cover 140 covers the second side 120b of the cartridge body 120. The second cover 140 and the first cover 110 may be formed by similar materials, and the similarities are not repeated here. In addition, the second cover 140 and the first cover 110 may be formed by the same material or different materials. In addition, the second cover 140 is bonded to the cartridge body 120 by using such as hot melting method, ultra-sound bonding technology or adhering method.

Referring to FIG. 5, a cross-sectional view along a direction 5-5' of FIG. 2 is shown. In the present embodiment, the sealing film 150 is strip-shaped. The sealing film 150 passes through the first cover 110 through the second through hole 122 of the cartridge body 120 and the first through hole 111 of the first cover 110.

The sealing film 150 penetrates the second through hole 122 and the first through hole 111 by way of reversely bending the sealing film 150. To put it in greater details, one terminal 151 of the sealing film 150 is reversely bended after sealing the liquid through hole 131, so that another terminal 152 of the sealing film 150 passes through the first cover 110 through the second through hole 122 and the first through hole 111. In addition, the sealing film 150 may seal the liquid through hole 131 by using hot melt method.

Figure 6:
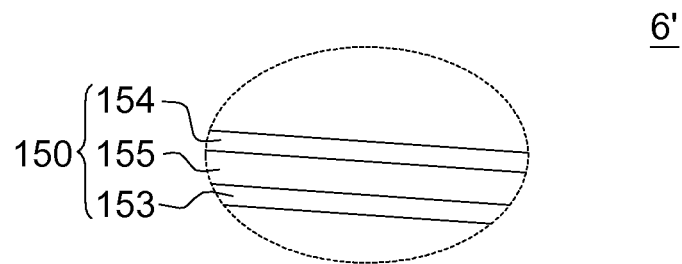
FIG. 6 shows a partial enlargement diagram of a portion 6' of FIG. 2.

Referring to FIG. 6, a partial enlargement diagram of a portion 6' of FIG. 2 is shown. The sealing film 150 is such as a multi-layer structure. For example, the sealing film 150 comprises a bonding layer 153, a metal layer 154 and an adhesive layer 155.

The bonding layer 153 seals the liquid through hole 131, and the adhesive layer 155 is formed between the bonding layer 153 and the metal layer 154 for bonding the bonding layer 153 to the metal layer 154. In an embodiment, the bonding layer 153 and the cartridge body 120 may be formed by the same material such as polypropylene (PP) or polyethylene terephthalate (PET). During the hot melt process, after the bonding layer 153 reaches the glass transition temperature, the bonding layer 153 may be bonded to the liquid storage box 130.

The metal layer 154 is formed by a metal having superior thermal conductivity such as aluminum or other metal. Due to the superior thermal conductivity, the thermal conductive layer 154, without contacting the sealing film 150, may transmit the heat to the bonding layer 153 via the metal layer 154 for heating the bonding layer 153.

Figure 7:
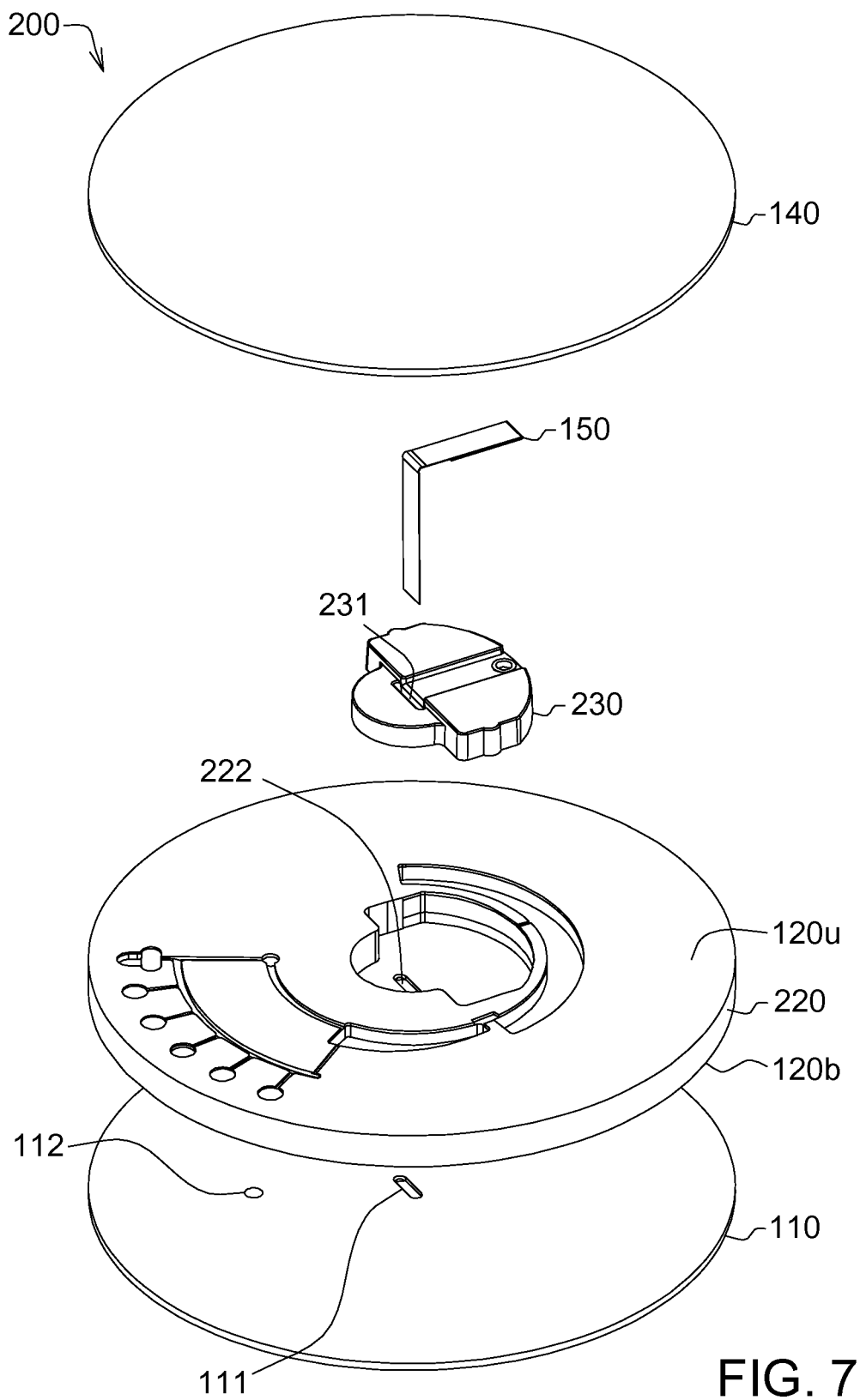
FIG. 7 shows an explosion diagram of an analysis cartridge according to another embodiment of the invention.

Referring to FIG. 7, an explosion diagram of an analysis cartridge according to another embodiment of the invention is shown. The analysis cartridge 200 comprises a first cover 110, a cartridge body 220, a liquid storage box 230, a second cover 140 and a sealing film 150.

The first cover 110 covers a second side 120b of the cartridge body 220. The cartridge body 220 further has a second through hole 222. In comparison to the liquid storage box 130, the liquid storage box 230 has a third through hole 231. The second cover 140 covers the first side 120u of the cartridge body 220.

Figure 8:
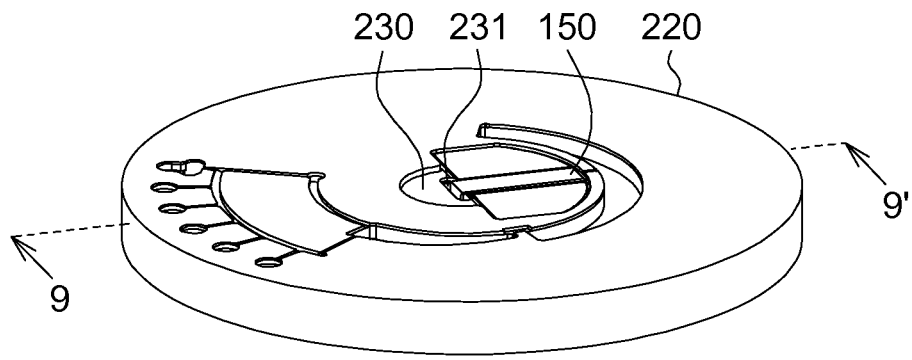
FIG. 8 shows an assembly diagram of a cartridge body, a liquid storage box and a sealing film of FIG. 7.
Figure 9:
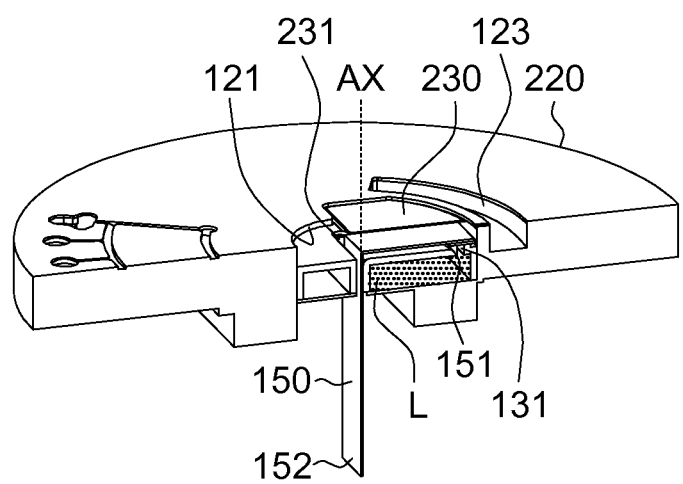
FIG. 9 shows a cross-sectional view along a direction 9-9' of FIG. 8.

Referring to FIGS. 8 and 9. FIG. 8 shows an assembly diagram of a cartridge body, a liquid storage box and a sealing film of FIG. 7. FIG. 9 shows a cross-sectional view along a direction 9-9' of FIG. 8.

The liquid storage box 230 is contained within the accommodation portion 121 of the cartridge body 220. One terminal 151 of the sealing film 150 seals the liquid through hole 131, and another terminal 152 of the sealing film 150 passes through the first cover 110 through the third through hole 231, the second through hole 222 and the first through hole 111 (the first through hole 111 and the first cover 110 are not illustrated in FIGS. 8 and 9).

When analysis is performed, the operator may pull another terminal 152 of the sealing film 150 for exposing the sealed liquid through hole 131. Then, after the analysis cartridge 100 is loaded into an analyzer (not illustrated), the analyzer drives the analysis cartridge 100 to rotate around the axis AX, so that the diluent L stored in the liquid storage box 230 is driven by the centrifugal force to flow to the liquid channel 123 through the exposed liquid through hole 131. In addition, the axis AX is such as the center of the cartridge body 220.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An analysis cartridge, comprising:
    a cartridge body having an accommodation portion and a first side and a second side opposite to the first side;
    a first cover covering the first side or the second side of the cartridge body and having a first through hole;
    a liquid storage box disposed within the accommodation portion and having a liquid through hole;
    a sealing film used for sealing the liquid through hole of the said liquid storage box and passing through the first through hole of the first cover, wherein the liquid through hole is exposed by removing the sealing film.

2. The analysis cartridge according to claim 1, wherein the first cover covers the first side of the cartridge body, and the analysis cartridge further comprises:
    a second cover covering the second side of the cartridge body.

3. The analysis cartridge according to claim 1, wherein the liquid storage box comprises:
    a box body having a terminal surface, a liquid storage tank and a tank bottom, wherein the liquid storage tank extends to the tank bottom from the terminal surface, and the liquid through hole penetrates the tank bottom; and
    a tank cover covering an opening of the liquid storage tank which is formed on the terminal surface of the box body.

4. The analysis cartridge according to claim 1, wherein the sealing film comprises:
    a bonding layer sealing the liquid through hole;
    a metal layer; and
    an adhesive layer formed between the bonding layer and the metal layer.

5. The analysis cartridge according to claim 1, wherein a terminal of the sealing film is bended after sealing the liquid through hole, such that another terminal of the sealing film passes through the first through hole of the first cover.

6. The analysis cartridge according to claim 1, wherein the cartridge body has a liquid channel and a reaction chamber, and the liquid channel interconnects with the reaction chamber and the accommodation portion of the said cartridge body.

7. The analysis cartridge according to claim 6, wherein the liquid channel has a liquid accumulation tank, a first distribution channel and a second distribution channel, the first distribution channel and the second distribution channel are connected to the liquid accumulation tank, and a distance between the first distribution channel and an axis of a center of the analysis cartridge is larger than that between the second distribution channel and the axis.

8. The analysis cartridge according to claim 1, wherein the cartridge body further has a second through hole, the sealing film passes through the second through hole of the cartridge body and the first through hole of the first cover.

9. The analysis cartridge according to claim 1, wherein the first cover covers the second side of the analysis cartridge, the cartridge body further has a second through hole, the liquid storage box has a third through hole, the sealing film passes through the third through hole, the second through hole and the first through hole.

10. The analysis cartridge according to claim 1, wherein the sealing film is a strip-shaped sealing film.

11. An analysis cartridge, comprising:
    a cartridge body having an accommodation portion and a first side and a second side opposite to the first side;
    a liquid storage box disposed within the accommodation portion and having a liquid through hole, wherein the liquid storage box comprises a liquid storage tank having an opening and a tank cover covering the opening of the liquid storage tank, and the liquid through hole is formed on the bottom of the liquid storage tank;
    a sealing film used for sealing the liquid through hole, wherein the liquid through hole is exposed by removing the sealing film; and
    a cover, wherein the cover covers the first side or the second side of the cartridge body and has a cover through hole, and the sealing film passes through said cover through hole.

12. The analysis cartridge according to claim 11, wherein the liquid through hole of the liquid storage box faces the first side of the cartridge body.

\* \* \* \* \*